United States Patent [19]

Lehmer

[11] Patent Number: 5,387,180
[45] Date of Patent: Feb. 7, 1995

[54] ULTRASONIC FREQUENCY SYNTHESIZER FOR PHACO SURGERY

[75] Inventor: Donald E. Lehmer, Berkeley, Calif.
[73] Assignee: Allergan, Inc., Irvine, Calif.
[21] Appl. No.: 65,141
[22] Filed: May 20, 1993
[51] Int. Cl.⁶ .............................................. A61H 1/00
[52] U.S. Cl. .................................. 601/2; 128/660.01; 310/316
[58] Field of Search ........ 128/24 AA, 660.01, 662.05; 604/22; 310/316–319; 601/2

[56] References Cited

U.S. PATENT DOCUMENTS

| | | | |
|---|---|---|---|
| 4,559,826 | 12/1985 | Nelson | 310/317 |
| 4,689,515 | 8/1987 | Benndorf et al. | 310/316 |
| 4,966,131 | 10/1990 | Houghton et al. | 128/24 AA |
| 5,276,376 | 1/1994 | Puskas | 310/316 |
| 5,318,570 | 6/1994 | Hood et al. | 601/2 X |

FOREIGN PATENT DOCUMENTS

| | | | |
|---|---|---|---|
| 0359217 | 3/1990 | European Pat. Off. | 604/22 |
| 0424685 | 5/1991 | European Pat. Off. | |
| WO921124 | 11/1992 | WIPO | |

OTHER PUBLICATIONS

1982 Ultrasonics Symposium Proceedings Oct. 1982 San Diego pp. 696–699.

*Primary Examiner*—Lee S. Cohen
*Assistant Examiner*—Brian L. Casler
*Attorney, Agent, or Firm*—Walter A. Hackler

[57] ABSTRACT

A method of generating wave forms for a phaco surgical handpiece, with each wave form having a different frequency includes storing a plurality of sets of digital information, each set corresponding to a different specific frequency and selecting a set of digital information in response to an input corresponding to a resonance frequency of said phaco surgical handpiece. Thereafter selected digital information is read in a manner producing a digital output having a corresponding frequency equal to or lower than the frequency corresponding to the selected set of digital information. Subsequently, the digital output is converted into an analog wave form for driving said phaco surgical handpiece.

17 Claims, 2 Drawing Sheets

ULTRASONIC FREQUENCY SYNTHESIZER FOR PHACO SURGERY

The present invention generally relates to phaco emulsification of a lens in a human eye through the use of an ultrasonically driven handpiece and is more particularly directed to a method of an apparatus for providing driving frequencies for such handpieces.

Handpieces for phaco emulsification generally include an ultrasonically vibrated hollow needle, the tip of which is used to disintegrate, or emulsify, the hard nuclear material found in cataract lenses. The handpiece also typically includes a tubal channel connected to the bore of said hollow needle for aspirating the emulsified cataract lens material from the eye.

The hollow needle of the handpiece is typically driven or excited along its longitudinal axis by the piezoelectric effect in crystals created by a large AC voltage. The motion of the driven crystal is amplified by a mechanically resonant system within the handpiece such that the motion of the needle connected thereto is directly dependent upon the frequency at which the crystal is driven, with a maximum motion occurring at the resonant frequency of the mechanically resonant system. The resonant frequency is naturally, in part, dependent upon the mass of the needle interconnected therewith, which is to be vibrated. The resonant frequency of a specific probe is therefore a variable, dependent upon the characteristics of the mechanical resonant system, the replaceable needle selected, and upon the loading on said needle occurring during the emulsification process.

It is currently assumed that once the frequency of resonance of the handpiece is found, maximum motion is produced when the handpiece is driven at a constant frequency close to the resonant frequency. This produces a maximum longitudinal motion of the tip of the needle, and importantly, minimizes the amount of heating of the handpiece by operating said handpiece at the frequency of highest efficiency.

Because of the specific ultrasound requirements for handpieces used in phaco surgery, special frequency synthesizers and drivers have been designed therefor. Heretofore, voltage controlled oscillators have been utilized with a feedback from the handpiece used to select a desired frequency. Because of this, analog feedback loop instability in the output may occur.

A synthesizer designed in accordance with the present invention overcomes this problem and is based upon generating frequencies digitally to maintain a constant frequency. The method in accordance with the present invention includes a means for selecting a specific frequency from a fixed set of frequencies. Thus, the actual sinusoidal output is synthesized digitally rather than being generated by an analog circuit.

This method and apparatus actually generates a sinusoidal output by converting a digital representation of a sine wave to the analog domain. Thus, the output is instantly stable in that the synthesizer selects frequencies from said set of available frequencies in ascending or descending order until the desired frequency is found.

SUMMARY OF THE INVENTION

An ultrasonic frequency synthesizer for a phaco surgery handpiece in accordance with the present invention generally includes means for storing a plurality of sets of digital information with each set comprising a specific frequency. Means are provided for selecting one of the sets of digital information, and additionally, means are provided for changing the frequency corresponding to the selected set of digital information. These two means provide for two methods, used in combination, to extend the range of the synthesizer. The means for selecting a set of digital information provides a fine method to change frequency while the means for changing the frequency of a selected set provides a coarse method to change frequency. In accordance with the design, the number of available frequencies is the product of the available frequencies by each means.

Additional means are provided for converting the changed selected set of digital information into an analog sine wave for driving the phaco surgery handpiece via a power amplifier. This apparatus is particularly suitable for phaco surgery handpieces. Because a handpiece can have a resonance at frequencies different from the design frequency, it is desirable to utilize a synthesizer, in accordance with the present invention, such as one having a limited range of frequency output.

A method in accordance with the present invention for generating wave forms for a phaco surgical handpiece generally includes the steps of storing a plurality of sets of digital information with each set corresponding to a different specific frequency.

In order to generate an output of a specific frequency, selected from a set of available frequencies, a method in accordance with the present invention selects a set of digital information in response to a control input corresponding to the resonant frequency of a phaco surgical handpiece. Thereafter, the selected digital information is read in a manner producing a digital output having a corresponding frequency equal to or lower than the frequency corresponding to the selected set of digital information. The digital output is then converted into an analog wave form for driving a phaco surgical handpiece.

More particularly, in accordance with the present invention, the step of reading the selected set of digital information comprises reading said information in a discontinuous manner. Still more particularly, the discontinuous manner comprises suspending the reading of the selected set of digital information to cause said digital information to be maintained for a specific period of time. The length of time of said suspension is a digitally selected value and comprises one of the two frequency changing means. Further, the suspension of the reading of the digital information is timed in order to produce a constant analog output, or flat spot in the analog wave form corresponding to the digital output.

Preferably, the constant analog output is timed in order to produce a flat spot in each crest of the analog wave form corresponding to the digital output. Further, the suspended reading of the stored digital information results in a frequency reduction of the digital output of up to about 12%. This is adequate to cover the frequency range needed by a typical phaco handpiece.

In order to provide a smooth change in frequency of the digital output, the step of selecting a set of digital information and the amount of suspension time for the reading of the digital information is performed in a binary manner, with the set of digital information being selected by the lower order bits and the suspension time being selected by the higher order bits.

BRIEF DESCRIPTION OF THE DRAWINGS

The advantages and features of the present invention will be better understood by the following description when considered in conjunction with the accompanying drawings in which.

DETAILED DESCRIPTION

Figure 1:
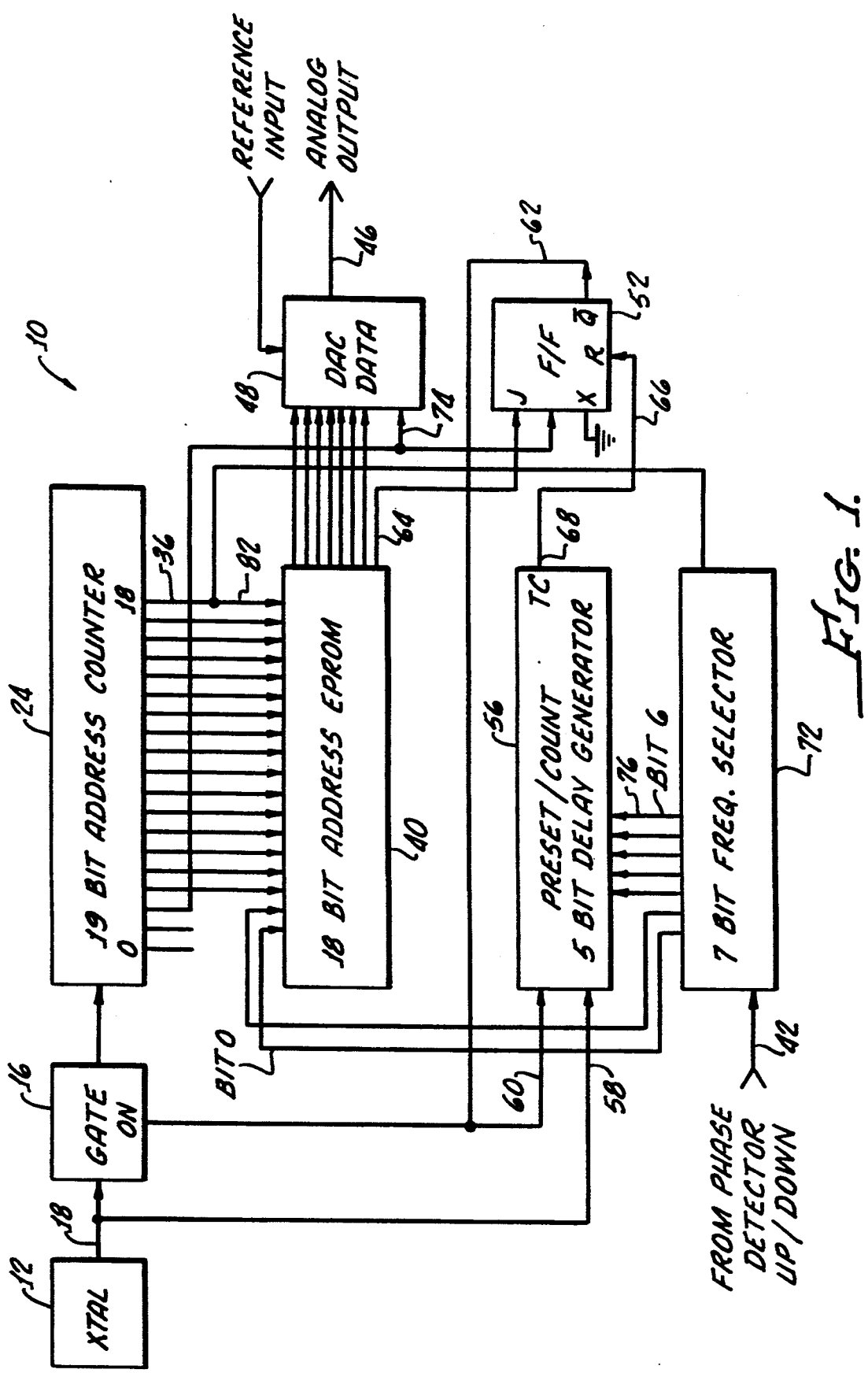
FIG. 1 is a functional block diagram of the ultrasonic frequency synthesizer in accordance with the present invention and illustrating the method of the present invention.

Turning now to FIG. 1, the synthesizer 10 in accordance with the present invention is represented by eight functional blocks, with each block comprising a conventional state-of-the-art circuitry of typical design and components for producing the function represented by each block as hereinafter described.

A conventional crystal oscillator 12 is provided for timing all the events in the method and apparatus of the present invention and is responsible for the stability of the synthesizer 10 output. Suitable for the present invention is a crystal oscillator 12 having a frequency .output of 25.175 MHz.

Figure 2:
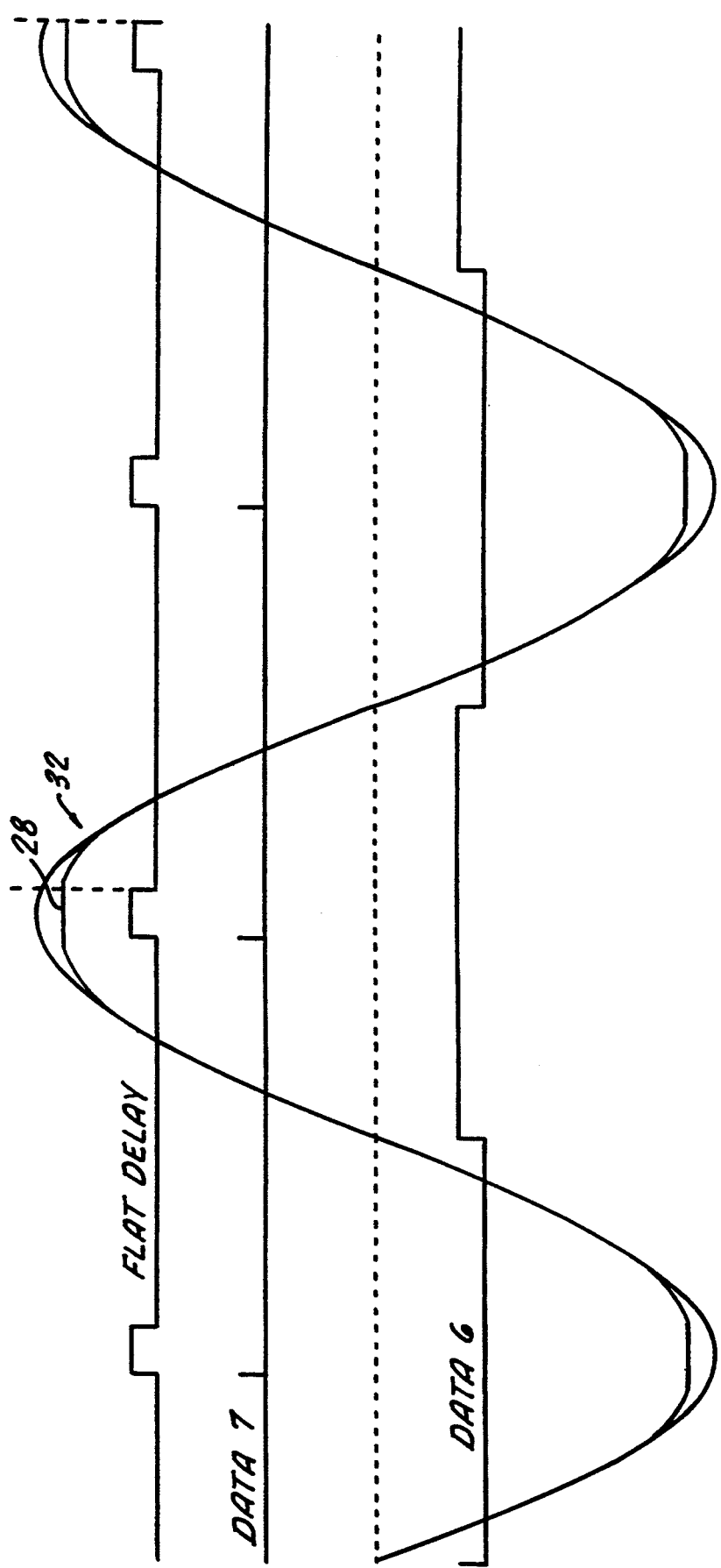
FIG. 2 is a representation of the lowest frequency analog sinusoidal wave form complete with said constant analog output, or flat spot, at the crest generated in accordance with the present invention and an overlaid representation of an analog sinusoidal wave form devoid of the constant analog output at the crest generated in accordance with the present invention.

As hereinafter described in greater detail, a gate 16 controls the output 18 of the crystal oscillator 12. The gate 16 either allows the clock to increment the address counter 24 or prevent the address counter 24 from incrementing. As also hereinafter discussed in greater detail, the purpose of this gated control is to provide a means for generating a flat spot 28 on the output 32 of the synthesizer 10 as shown in FIG. 2.

The address counter 24 is a conventional 19 stage binary counter and provides a well known method of dividing the clock 12 input into frequencies which are lower by a factor of 2 for each stage. The last stage output 36 requires 524,288 clock pulses before it completes a cycle. The number of clock pulses is calculated by taking 2 to the 19th power.

If the gate 16 does not prevent the address counter 24 from incrementing, the complete cycle of the 19 stages occurs about 48 times a second, i.e., 25,175,000 divided by 524,288.

A plurality of sets of digital information with each set corresponding to a specific different frequency is stored in the EPROM (erasable read only memory) 40, which has an 18-bit address field containing 262,144 bytes of data, which are arranged in 4 pages of 65,536 bytes each. Each of these sets is selected in response to a control input 42 corresponding to a resonance frequency of a phaco surgical handpiece (not shown). With a specific set selected, the address counter 24 scans the data in one of the 4 pages about 48 times per second.

The digital information stored in the EPROM 40 will generate a sine wave analog output 46 through the use of a conventional video digital-to-analog converter 48. Each page of the EPROM 40 contains an integral number of sine wave cycles, starting and ending with the analog output at a zero crossing. Thus, for a page containing 1,025 cycles of a sine wave; it will be generated about 48 times a second, which in turn generates a frequency of 49,218 Hz (1,025 cycles times 48 scans per second), which is the highest frequency for the embodiment shown in FIG. 1.

The other 3 pages of the EPROM 40 contain 1,024, 1,023, and 1,022, respectively, cycles of sine wave data. It can be seen that selecting a page with 1,024 cycles will generate a slightly lower frequency than the 1,025 cycle page, with a resolution of about one part in 1,000, producing a change in frequency of about 50 Hz per page.

As hereinabove noted, there are 65,536 bytes in one complete pass through one page of the EPROM 40 addresses. If there are 1,024 cycles of sine wave data in the selected page, then there are exactly 64 bytes per cycle (65,536/1,024). With 64 bytes per cycle, the data is zero every 32 bytes. Note that if the 1,025 cycle page is selected, there are 63.93756 bytes per cycle. This causes the data to be slightly positive at the end of the first 64 bytes, since the sine wave has already started into the next cycle. The data will be more positive after 64 more bytes, until one complete cycle is added after 1,024 sets of 64 bytes (65,536 bytes).

A similar process occurs for the 1,023 and the 1,022 cycle pages, except one or two cycles, respectively, are subtracted.

Turning again to the EPROM 40, 7 of the 8 bits in each byte of data are latched onto the video digital-to-analog converter 48, the data representing the sine wave, and the highest order bit is latched by a single bit J/K type latch 52, a marker near the crest. Both said digital-to-analog converter and latch are clocked by the falling edge of the 3rd stage of the address counter 24. This stage changes from a one to a zero for each change in address of the EPROM 40. This provides a means for clocking new data from the EPROM 40 just before the next byte is addressed, thereby disregarding the time when the EPROM data is changing value between addresses.

The delay generator 56 is constructed from a counter similar to the address counter 24. The delay generator 56 is clocked by the crystal oscillator 12 via input 58 and functions to suspend the operation of the address counter 24. When the address does not change to the EPROM 40, and the digital-to-analog converter 48 and the J/K latch 52 clock stop. This has the effect of maintaining the last data read from the EPROM 40 until the address counter 24 is no longer suspended. This has the effect of changing the digital data to produce a digital output having a frequency lower than the frequency corresponding to the selected set of digital information.

That is, this produces a discontinuous reading of the digital information in the EPROM 40. Since the addresses do not change during the suspension of counting, a flat spot 28 is generated at each crest of the sine wave 32.

The delay generator 56 is constructed from a digital counter which includes an input 60 capable, when true, of holding the counter preset in a state determined by the parallel inputs 76 or capable, when false, of allowing the counter to increment. The source of input 60 is an output 62 of the latch 52.

Thus, the latch 52 controls the input 60 to the delay generator 56 and also prevents the address counter 24 from advancing by the gate 16. The latch 52 may be generally of the J/K type, such as National Semiconductor's Dual Negative-Edge-Triggered Master-Slave J/K Flip-Flop #54LS112/DM. In this application, with K made false, the latch 52 will set if J is true, and a falling edge occurs at the clock input. If J were to become false, and a clock occurs, the state would not change. The only way to clear the J/K latch 52 is to reset it by its reset input 66 connected to the terminal count output 68 of the delay generator 56.

The data to the J input of the latch 52 is connected to the highest order bit 64 in the EPROM 40. Said bit 64 is programmed to be true for only one byte near each crest of the sine wave data.

The J/K latch 52 is set when the highest order bit 64 is true, and a negative clock occurs. This stops the address counter 24, via gate 16 and allows the delay generator 56 to increment from the state supplied from a frequency selector 72. Note that this occurs in all cases except when the frequency selector 72 state is equal to the maximum value (all true). In this case the terminal count of the delay generator counter 56 is true and therefore holds the J/K latch 52 reset. This causes no delay since reset over-rides the possibility of setting the J/K latch 52. In all other cases, the delay generator 56 counter increments to the terminal count and resets the J/K latch 52. This allows normal counting at the address counter 24 to proceed.

Note that when the J/K latch resets, the delay generator 56 reverts to the preset mode, presetting the value supplied by the frequency selector 72, ready to operate at the next crest of the sine wave. Note that the J/K latch was chosen over the conventional D type latch since the delay of the delay generator 56 can be less than, equal to, or greater than the duration of the highest order bit (8 clocks) of the EPROM 40. If the delay is greater, the D type latch would reset on the next clock, but the J/K latch will not reset, since K is false.

The preset input from the frequency selector 72 is capable of generating a delay from 0 to 31 clock periods by controlling the preset state of 5 bits 76 forming the preset input of the delay generator 56. The lowest frequency is generated by using the EPROM 40 page with 1,022 cycles and the maximum delay, 31 clocks per crest, of the delay generator 56. This removes 63,364 (1,022 times 31 times 2) clocks, requiring 587,652 (524,288 plus 63,364) clocks to complete 1,022 cycles or 43,782 Hz (25,175,000 divided by 587,625 times 1,022). Without the delay, the frequency would be higher by about 12% (25,175,000 divided by 524,288 times 1,022), or 49,074 Hz.

Thus the reading of the digital information produces a digital output having corresponding frequency equal to or lower than the frequency corresponding to the selected set of digital information. Since there are 4 pages of stored information and 32 possible delays, the resulting total of available frequencies is 128 (4 times 32). These are shown in Table 1 in which the left column is the highest frequency for each delay, and the 4 columns list the frequency reduction for each EPROM page. It should also be appreciated that the synthesizer 10 is unique in that the frequency may be changed after one scan (20.8 milliseconds) without waiting for feedback, and without a transient in the output wave form.

TABLE I

| Frequency | 1025 Cycles | 1024 Cycles | 1023 Cycles | 1022 Cycles |
|---|---|---|---|---|
| 49218 KHz |  | 48 Hz | 48 Hz | 48 Hz |
| 49026 KHz | 47 Hz | 47 Hz | 47 Hz | 47 Hz |
| 48836 KHz | 47 Hz | 47 Hz | 47 Hz | 47 Hz |
| 48647 KHz | 46 Hz | 46 Hz | 46 Hz | 46 Hz |
| 48460 KHz | 46 Hz | 46 Hz | 46 Hz | 46 Hz |
| 48274 KHz | 46 Hz | 46 Hz | 46 Hz | 46 Hz |

TABLE I-continued

| Frequency | 1025 Cycles | 1024 Cycles | 1023 Cycles | 1022 Cycles |
|---|---|---|---|---|
| 48090 KHz | 45 Hz | 45 Hz | 45 Hz | 45 Hz |
| 47907 KHz | 45 Hz | 45 Hz | 45 Hz | 45 Hz |
| 47725 KHz | 45 Hz | 45 Hz | 45 Hz | 45 Hz |
| 47545 KHz | 44 Hz | 44 Hz | 44 Hz | 44 Hz |
| 47366 KHz | 44 Hz | 44 Hz | 44 Hz | 44 Hz |
| 47188 KHz | 44 Hz | 44 Hz | 44 Hz | 44 Hz |
| 47012 KHz | 43 Hz | 43 Hz | 43 Hz | 43 Hz |
| 46837 KHz | 43 Hz | 43 Hz | 43 Hz | 43 Hz |
| 46664 KHz | 43 Hz | 43 Hz | 43 Hz | 43 Hz |
| 46491 KHz | 42 Hz | 42 Hz | 42 Hz | 42 Hz |
| 46320 KHz | 42 Hz | 42 Hz | 42 Hz | 42 Hz |
| 46150 KHz | 42 Hz | 42 Hz | 42 Hz | 42 Hz |
| 45982 KHz | 41 Hz | 41 Hz | 41 Hz | 41 Hz |
| 45814 KHz | 41 Hz | 41 Hz | 41 Hz | 41 Hz |
| 45648 KHz | 41 Hz | 41 Hz | 41 Hz | 41 Hz |
| 45483 KHz | 41 Hz | 41 Hz | 41 Hz | 41 Hz |
| 45319 KHz | 40 Hz | 40 Hz | 40 Hz | 40 Hz |
| 45157 KHz | 40 Hz | 40 Hz | 40 Hz | 40 Hz |
| 44995 KHz | 40 Hz | 40 Hz | 40 Hz | 40 Hz |
| 44835 KHz | 39 Hz | 39 Hz | 39 Hz | 39 Hz |
| 44676 KHz | 39 Hz | 39 Hz | 39 Hz | 39 Hz |
| 44518 KHz | 39 Hz | 39 Hz | 39 Hz | 39 Hz |
| 44361 KHz | 39 Hz | 39 Hz | 39 Hz | 39 Hz |
| 44205 KHz | 38 Hz | 38 Hz | 38 Hz | 38 Hz |
| 44051 KHz | 38 Hz | 38 Hz | 38 Hz | 38 Hz |
| 43897 KHz | 38 Hz | 38 Hz | 38 Hz | 38 Hz |

The frequency selector 72 is a 7-bit reversible counter capable of counting in the forward or reverse direction, dependent upon the up/down control 42. The falling edge of the last EPROM address 82 causes the frequency selector counter 72 to increment or decrement, dependent upon the state of the up/down input 42. The last address 82 has a frequency of about 48 Hz (25,125,000 divided by 524,288), the maximum rate of frequency change.

This causes the frequency selector 72 to change state at the completion of the address scan in the EPROM 40. This, in turn, changes the frequency only after a complete scan, when the data is at zero crossing, to prevent transients when the frequency is changed. The 5 high order bits determine the delay of the delay generator 72, and the 2 low order bits select one of the four EPROM 40 pages.

In operation this allows the frequency selector 72 to first change the EPROM pages through the 4 possible pages, changing the frequency slightly as hereinabove noted, and then change the delay. The effect of adding one more delay changes the frequency an amount just proper to use the four EPROM pages again for a smooth change of frequency.

The desired frequency is selected by controlling the direction of counting of the frequency selector 72 via the up/down input 42. This control is from a phaco surgery handpiece (not shown) through a phase detector (not shown), which is not part of the present invention.

The clock signal 18 causes the address counter 24 to increment, scanning the data in the EPROM 40 to be converted to an analog equivalent by the digital-to-analog converter 48. This generates a sinusoidal wave form with a peak value equal to the reference input 74. This reference input 74 allows the amplitude of the sine wave to be changed to a less than the maximum without a loss in wave shape, a requirement to control the power to the phaco surgery handpiece. The sine wave is generated by intentional programming of the EPROM 40 to contain a digital representation of 1,025, 1,024, 1,023 or 1,022 complete cycles of a sine wave, recorded in the 4 pages of EPROM 40. The number of cycles desired, and hence the frequency, is controlled by whichever page is selected by the frequency selector 72 and provides a fine method of changing frequency.

A further reduction in frequency is provided by discontinuous operation of the address counter 24, where the counter is not always incrementing. Rather, it is scheduled to stop at, or near, the crest of each wave in order to reduce the frequency digitally by creating a flat spot 28 on wave form 32 (see FIG. 2). The suspension of counting is scheduled by the high order bit of EPROM 40 which sets a J/K latch 52. This provides a coarse method of changing frequency.

The data in the EPROM 40 is programmed such that the high order bit is true for only one byte near the crest of the recorded wave. When the J/K latch 52 is set, the address counter 24 is stopped by gate 16. This stops the change in address to the EPROM 40 and holds the data at the crest of the generated wave. The setting of the J/K latch 52 also changes the delay generator 56 from the preset mode, where the counter is held in a state of the frequency selector 72 to an increment mode. This causes the delay generator 56 to count and reset the J/K latch 52 when it reaches its maximum state. This, in turn, enables the address counter 24 and presets the delay generator 56 to the state of the frequency selector 72.

Since there are 8 clocks per change in EPROM address and about 64 EPROM bytes per cycle, there are about 512 clocks per cycle. Suspending the address counter for 1 clock at both crests would therefore reduce the frequency by about 1 part in 256. Changing the EPROM 40 by one page changes the frequency by about 1 part in 1,024 and hence, the combining of these two frequency adjustment methods allows for 0.1% resolution and a 12% range of frequency change. The two methods are combined by connecting the selection of the set of digital information to the lower order bits of a binary control byte 76 and the selection of the amount of delay from the delay generator 56 to the higher order bits of said byte 76. In this manner, the set of digital information is selected for fine changes in frequency, and when the combinations are exhausted, the sequence is repeated with a different delay from the delay generator 56.

When the frequency selector 72 is in the 0 state, the lowest frequency page of EPROM 40 is selected (1,022) and the number of clock periods for the delay generator 56 is a maximum of 31. This due to the fact that the 5 bit delay generator counter starts at zero and must count through 31 states to reset the J/K latch and start the address counter 24 again. This causes the lowest possible frequency. As the state of the frequency selector 72 is incremented, the pages of the EPROM 40 are selected in ascending cycle order, then recycled with a reduction in delay in the delay generator 56 by two clocks per cycle. These two frequency changing methods operate in concert where the EPROM pages act as a vernier to produce a smooth change in frequency. The maximum frequency occurs when there is no delay and the page with the highest frequency is selected (1,025).

As hereinabove described, the method in accordance with the present invention includes the generation of a wave form having a frequency which is selected by two methods. A coarse adjustment is provided by changing frequency using crest delay, and a fine adjustment is provided by selecting different EPROM pages 40.

FIG. 2 shows the timing relationship between the data in bit 6 and 7 of EPROM 40 and the worst case flat spot output wave form. The shape of said wave form is very similar to the shape of the overlaid sinusoidal wave form, even though the EPROM 40 data to the digital-to-analog converter is for a wave from without the delay. The flat spot is typically not noticeable after passing through the power amplifier.

Although there has been hereinabove described a ultrasonic frequency synthesizer for phaco surgery in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A method of generating wave forms for a phaco surgical handpiece, each wave form having a different frequency, said method comprising the steps of:
   storing a plurality of sets of digital information, each set corresponding to a different specific frequency;
   selecting a set of digital information in response to an input corresponding to a resonance frequency of said phaco surgical handpiece;
   reading said selected digital information in a manner producing a digital output having a corresponding frequency equal to or lower than the frequency corresponding to the selected set of digital information; and
   converting the digital output into an analog wave form for driving said phaco surgical handpiece.

2. The method according to claim 1, wherein the step of reading said selected digital information comprises the step of lowering the corresponding frequency approximately 12 percent.

3. The method according to claim 1 wherein the step of reading said selected digital information comprises reading selected digital information in a discontinuous manner.

4. The method according to claim 3 wherein the discontinuous manner comprises suspending the reading of the selected digital information in order to cause repeated digital readings in the digital output.

5. The method according to claim 4 wherein the repeated digital readings are timed in order to produce a flat spot in the analog wave form corresponding to the digital output.

6. The method according to claim 5 wherein the repeated digital readings are timed in order to produce a flat spot in each crest of the analog wave form corresponding to the digital output.

7. The method according to claim 6, wherein the step of reading the stored digital information is repeated in order to provide a frequency adjustment to the digital output of up to about 12 percent.

8. The method according to claim 7 further comprising the step of selecting a set of digital information and selecting the number of repeated readings of the selected set of digital information in a binary sequence where the selection of the set of digital information is controlled by a lower order bits and the number of repeated readings of the selected digital data is selected by a higher order bits such that a change in said binary sequence provides a smooth change in frequency of the digital signal.

9. The method according to claim 8 wherein the step of storing a plurality of sets of digital information includes storing four sets of digital information.

10. A method of generating a set of wave forms for an ultrasonic phaco surgical handpiece, each wave form having a different frequency, said method comprising the steps of:
   storing a plurality of sets of digital information, each set corresponding to a different specific frequency and each set being convertible to an analog wave form;
   selecting a set of digital information in response to an input corresponding to a resonance frequency of said phaco surgical handpiece;
   also in response to said input modifying said selected digital information to
   produce a digital output having a corresponding frequency equal to or lower than the frequency corresponding to the selected set of digital information; and
   converting the digital output into one analog wave form having the handpiece resonance frequency.

11. The method according to claim 10 wherein the step of modifying said selected digital information comprises reading the selected digital information in a discontinuous manner.

12. The method according to claim 11 wherein the discontinuous manner comprises suspending the reading of the selected digital information in order to cause repeated digital reading in the digital output.

13. The method according to claim 12 wherein the repeated digital readings are timed in order to produce a flat spot in the analog wave form corresponding to the digital output.

14. The method according to claim 12 wherein the repeated digital readings are timed in order to produce a flat spot in each crest of the analog wave form corresponding to the digital output.

15. The method according to claim 14 where the step of storing a plurality of sets of digital information include storing four sets of digital information.

16. The method according to claim 15 further comprises the step of repeating the reading of each set of digital information in order to produce 32 different frequencies.

17. An ultrasonic frequency synthesizer for a phaco surgical handpiece, the synthesizer comprising:
   means for storing a plurality of sets of digital information, each set corresponding to a specific frequency;
   means for selecting a set of digital information corresponding to a resonance frequency of said phaco surgical handpiece;
   means for changing the frequency corresponding to the selected set of digital information; and
   means for converting the changed selected set of digital information into an analog sine wave for driving said phaco surgical handpiece.

* * * * *